United States Patent
Hommann et al.

(10) Patent No.: US 6,936,028 B2
(45) Date of Patent: Aug. 30, 2005

(54) COOLING DEVICE FOR AN INJECTION APPARATUS

(75) Inventors: Edgar Hommann, Grossaffoltern (CH); Christoph Rindlisbacher, Boll (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/379,436

(22) Filed: Mar. 4, 2003

(65) Prior Publication Data

US 2003/0171715 A1 Sep. 11, 2003

(30) Foreign Application Priority Data

Mar. 5, 2002 (CH) .............................................. 0377/02

(51) Int. Cl.[7] .............................................. A61F 7/12
(52) U.S. Cl. ...................................... 604/113; 604/112
(58) Field of Search ............................... 604/110, 112, 604/113–117, 264, 265

(56) References Cited

U.S. PATENT DOCUMENTS

| | | | |
|---|---|---|---|
| 4,725,265 A | | 2/1988 | Sairenji |
| 4,887,994 A | * | 12/1989 | Bedford .......................... 604/1 |
| 5,236,419 A | * | 8/1993 | Seney ......................... 604/112 |
| 5,370,629 A | | 12/1994 | Michel et al. |
| 5,417,662 A | | 5/1995 | Hjertman et al. |
| 5,795,336 A | * | 8/1998 | Romano et al. ............. 604/192 |
| 5,921,963 A | * | 7/1999 | Erez et al. .................. 604/192 |
| 6,213,977 B1 | | 4/2001 | Hjertman et al. |

* cited by examiner

Primary Examiner—Kevin C. Sirmons
(74) Attorney, Agent, or Firm—Dorsey & Whitney LLP

(57) ABSTRACT

An injection apparatus including a distally arranged cooling element, wherein the cooling element is detachably coupled to the injection apparatus or to a needle protecting device coupled to the injection apparatus, and a corresponding or complementary cooling container.

12 Claims, 2 Drawing Sheets a) b)

US 6,936,028 B2

COOLING DEVICE FOR AN INJECTION APPARATUS

CROSS-REFERENCE TO RELATED APPLICATION

This application claims priority to Swiss Application No. 2002 0377/02, filed on Mar. 5, 2002, the contents of which is hereby incorporated by reference.

BACKGROUND

The invention relates to cooling elements for injection apparatus and corresponding cooling containers.

Injection apparatus are known for example from U.S. Pat. No. 5,370,629 or are conventional syringes for administering medicines. Insulin-dependent diabetics, for example, have to be capable at any time of administering the required insulin using a syringe or injection pen. In this way, the skin is pierced by an injection needle (hereafter simply called a needle) when the insulin is injected.

The terms distal and proximal are used herein in such a way that distal means facing towards the patient and proximal means facing away from the patient.

It is known that the pain when a needle penetrates during an injection is substantially less or even absent if the skin is cooled or significantly cooled. Appropriately cooling the skin can reduce or even eliminate the pain when the needle penetrates into and under the skin.

As an example of a cooling device for anesthetizing the skin, U.S. Pat. No. 4,725,265 describes a syringe comprising a cooling device which sprays a coolant gas onto the surface of the skin before the injection is performed. The skin is only cooled before the injection, such that the effect noticeably wears off during lengthier injections. Since the application described is the injection of anesthetics, the anesthetic cancels out the wearing off of the cooling effect, which is not the case with other medicines. Furthermore, cooling this way requires a separate supply of coolant gas, such that for multiple injections a relatively large amount of coolant gas, and/or correspondingly large gas containers, are required. Another device, such as is shown in U.S. Pat. No. 5,921,963, cools the skin before and during the injection by means of a cooling plate connected to a cooling apparatus. In order to be able to use the cooling plate, the cooling apparatus must first be operated a certain period of time, a particular difficulty if the apparatus is supplied batteries for an out-patient application, especially since the batteries have a substantially lower output as compared to a mains supply. Due to its time-consuming initialization and the fact that an integrated cooling apparatus is constantly carried along with it, this structurally elaborate cooling device is also not suitable for out-patient injections performed by a non-professional.

It would be advantageous to conveniently and simply cool the skin during out-patient therapies. Ideally, the appropriate point on the skin is cooled to 12° C. or lower.

SUMMARY

The object of the present invention is to provide a simple cooling device for injections, wherein use is simple for non-professionals, does not require a time-consuming initialisation, an additional integrated cooling apparatus or assistance. Further objects are to provide a device which cools the skin before and during injection, and which can be discretely transported.

The cooling device in accordance with the invention, for injection apparatus, for cooling the skin consists of a cooling element and a corresponding cooling container. The cooling element is substantially a cooling accumulator, for example a highly heat-conductive metal part in the manner of a coin, which has a coupling element on or on the rim of its cover surface. Materials are known which are suitable as cooling accumulators, for example copper and copper alloys.

The cooling element of the present invention may be arranged either directly on the distal part of an injection apparatus or on a needle protector protection arrangement attached to the injection apparatus, such as is known, for example, from U.S. Pat. Nos. 5,417,662 or 6,213,977, but it may also be formed as a whole or integrated as a needle protection arrangement. Accordingly, the needle protection arrangement comprises an opening through which the needle penetrates directly into the skin during use.

If the cooling element is arranged on the needle protector, said element comprises a magnetic cover surface or a radial groove, and the needle protector comprises corresponding counter elements. Other detachable, positive-lock and/or frictional-lock connections between the cooling element and the injection apparatus or needle protector suggest themselves, but mostly require a small structural alteration to the cooling element and/or needle protection.

In some embodiments, the cooling element is designed to be coupled onto the front side of the needle protection arrangement, and then the cooling element has a passage as a continuation of the opening for the needle. The cooling element can therefore advantageously constantly cool the skin directly at the injection point, before and during the injection, without requiring an additional device or an assistant.

The cooling element can additionally possess a highly heat-conductive coating on the side which contacts the skin. Such a coating, for example a porous coating, has a specifically large surface, which favors heat conduction and consequently a quicker cooling of the skin. In some embodiments, the conductive coating preferably comprises an antibacterial surface or is impregnated with a disinfectant. In this way, evaporating the disinfectant results in a corresponding cooling of the cooling element and could simultaneously save on a separate step of disinfecting the injection point before using the injection apparatus.

In some embodiments, the cooling element of the present invention is stored in a cooling container. Since one preferred embodiment of the cooling elements is not larger than coins, a well insulating cooling container has a small size, suitable for transport, comparable to a powder box, even if—as intended—multiple cooling elements are carried along for multiple applications. In one embodiment, the preferred cooling container has a cooling core comprising a bore into which the cooling elements exactly fit, an insulation around the cooling core and a seal which is likewise insulating. In one preferred embodiment, the cooling core—together with the cooling elements—can be removed from the cooling container and cooled overnight in a freezer cabinet. It is equally possible to cool the cooling core with aid of a separate cooling apparatus, as with known systems used, for example, in cars or in the workplace. If, after use, the cooling elements are later to be used again, then the cooling container may have recesses, for example on the upper side of the seal, which can accommodate the cooling elements after use. In this way, the cooling container only has to be opened to take out a new, pre-cooled cooling element, whereby the accumulated coldness and the used cooling elements will not be lost. The cooling elements can, of course, also be cooled in a conventional freezer cabinet, in particular when the cooling element comprises an antibacterial surface or possesses an antibacterial coating.

When the cooling device in accordance with the invention is used, a cooling element is taken from the cooling container using the adapter or needle protection, and pressed onto the skin, before and during penetration, until the injection is complete. The conditions for cooling the skin in an out-patient, quick and pain-mitigating way, which can be performed by a non-professional without assistance, are therefore optimally fulfilled.

BRIEF DESCRIPTION OF THE DRAWINGS

Exemplary preferred embodiments of the cooling device injection apparatus in accordance with the invention and its use are described below with reference to the accompanying figures:

FIGS. 1a and 1b, is a horizontal section through each of first variant (a) and a second variant (b) of a cooling element;

FIGS. 2a and 2b is a partial view in a horizontal section through an injection apparatus comprising a first variant (a) of an adapter and in horizontal section through an injection apparatus comprising a second variant (b) of an adapter, each comprising a cooling element.

DETAILED DESCRIPTION

Figure 1:
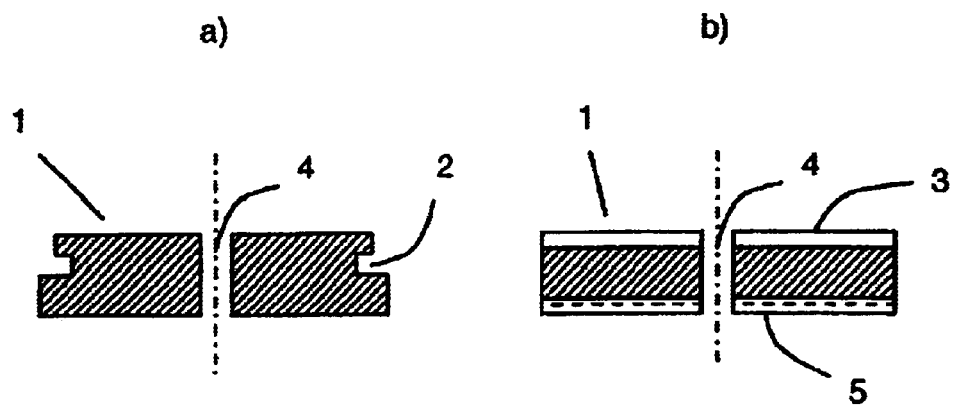
FIG. 1, including

FIG. 1a schematically shows a horizontal section of a cooling element 1 in the form of a coin. The cooling element 1 comprises a radial groove 2. In this embodiment, the preferred cooling element 1 has, in the center, a passage 4 for later forming a passage for the needle, during use.

Another preferred embodiment of a cooling element 1 in accordance with the invention is shown in FIG. 1b. The cover surface of the cooling element 1 comprises a magnetic surface 3 or the cooling element is magnetic as a whole. In addition, the counter surface can comprise a heat-conductive coating 5, for example a porous metallic tile, which can also absorb a disinfectant. The coating 5 can also be an antibacterial surface. This embodiment is also conceivable without a tile.

Figure 2:
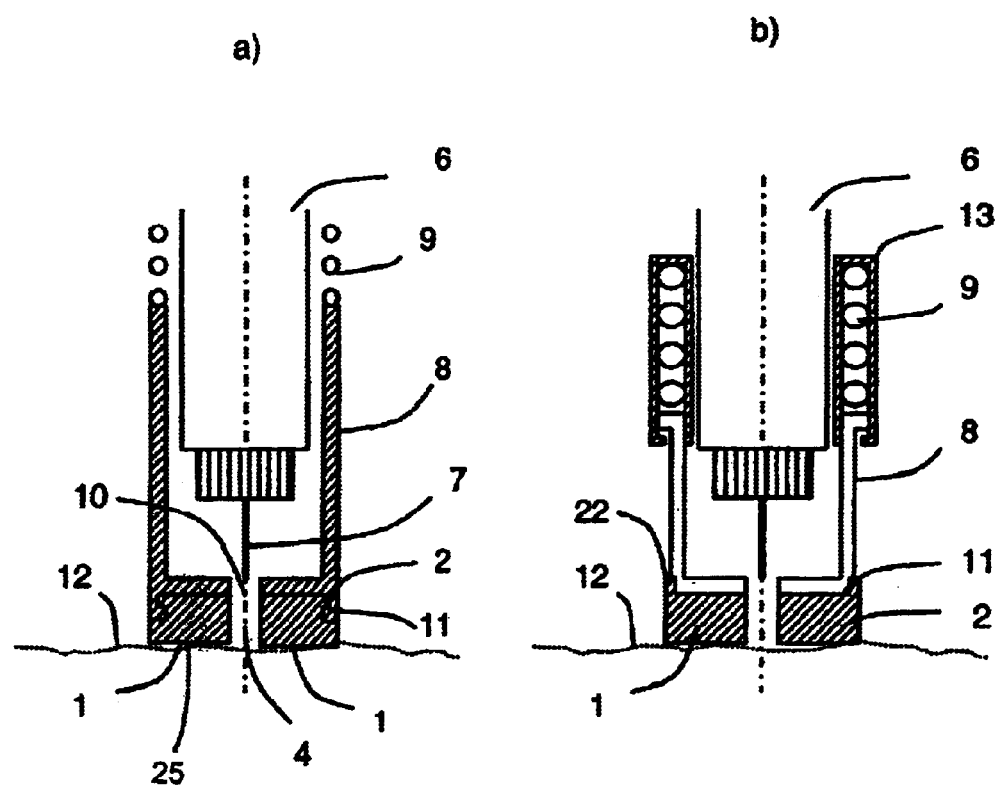
FIG. 2, including

FIG. 2a schematically shows a partial view of a horizontal section through an injection apparatus 6, for example an injection pen, onto the end of which a needle 7 is placed. The injection apparatus 6 has an adapter 8, or needle protection device, which is connected to the injection apparatus 6 via a spring and thus forms a needle protector movable along the injection apparatus 6, in the manner of a one-side cylinder partially closed on its facing side 25. The adapter 8 or said cylindrical needle protector has an opening 10 o its facing side 25 through which the needle 7 is advanced during an injection into and/or through the skin 12, as shown by a broken line. Situated on the rim of the facing side 25 of the adapter 8 is at least one counter element 11, e.g., in the form of a radial cam, which snaps into the radial groove 2 of a cooling element 11 in accordance with the invention. The cooling element 1, detachably fixed in this way to the facing side of the adapter 8, has a passage 4 for the needle 7, such as described in reference to FIG. 1. Consequently, the cooling element 1 can be placed onto the skin 12 before the injection using the injection apparatus 6 and held at the point until after the injection, without additional assistance being necessary.

Another partial view, in horizontal section, of an injection apparatus 6 may be seen in FIG. 2b, wherein, instead of a radial groove 2, the cooling element 1 comprises a protruding rim 22. For a detachable connection to the injection apparatus 6 or needle protection, the protruding rim 22 grips over the rim of the adapter 8 in an adhering or coupling frictional lock. The adapter 8 is not directly connected to the injection apparatus 6 via a spring 9, as shown in FIG. 2a. The spring 9 is arranged in a double-walled sleeve 13 which is plugged or clamped onto the injection apparatus 6. During the injection, the surface of the cylindrical adapter 8 is pushed into this sleeve 13 against the spring 9, said sleeve 13 not shifting in turn. The sleeve 13 can also be single-walled.

Figure 3:
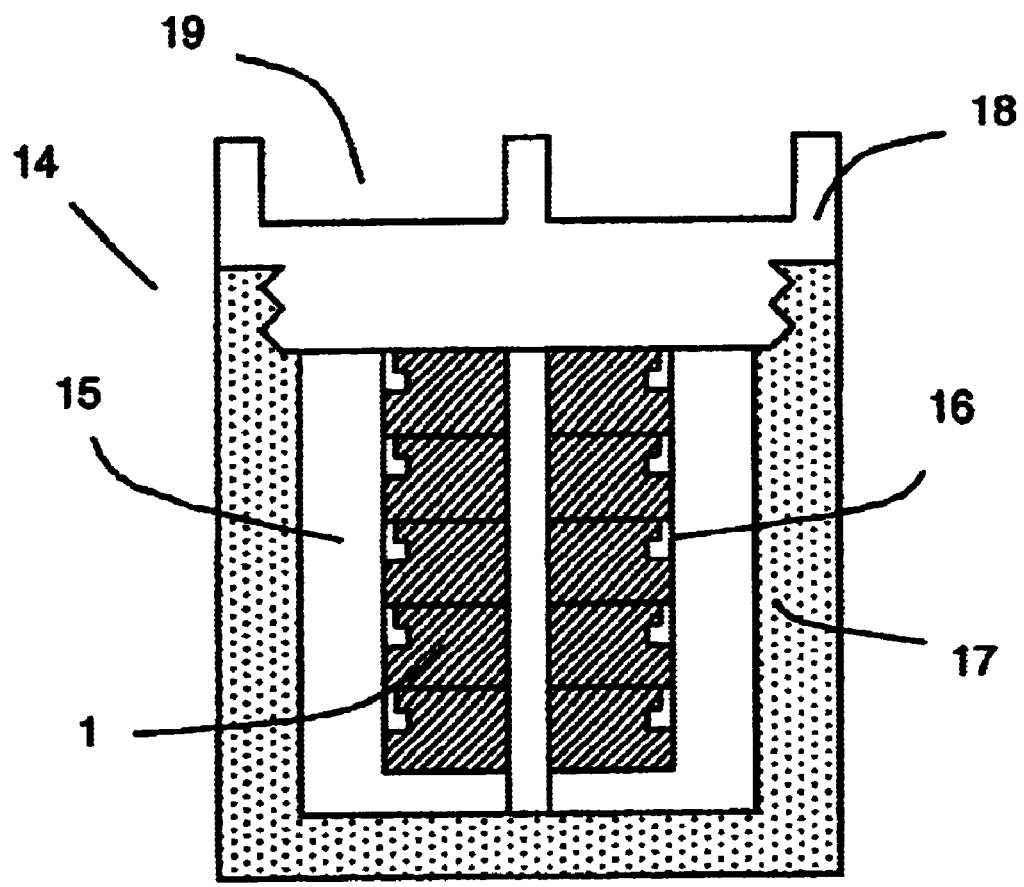
FIG. 3 is a horizontal section through a cooling container comprising multiple cooling elements.

FIG. 3 shows a central horizontal section through a cooling container 14 in accordance with the present invention. The cooling container 14 has a cooling core 15 comprising a bore 16 into which at least one cooling element 1 can be inserted in a substantially exact fit. The cooling core 15 consists of a material analogous to the cooling elements, in order to accumulate coldness as well as possible. In order that coldness is not lost, at least one insulator or insulating material 17 is arranged around the cooling core 15. It is advantageous if the cooling core 15 can be taken out of the insulation 17, so it can be cooled overnight in a freezer cabinet. In order that this is possible, the cooling container 14 has at least one seal 18 in its insulation 17, said seal 18 likewise providing an insulating seal for the interior space of the cooling container 14. In order to take a cooling element 1 out of the cooling container 14, the seal 18 is opened and a cooling element 1 is taken out using the adapter (not shown), simply by the two parts coupling onto each other. It is advantageous if, once a cooling element 1 has been used, it is not placed back in the cooling container 14 again, otherwise valuable coldness is lost. Therefore, in accordance with the invention, the cooling container 14 has recesses 19, for example in the seal 18, which can accommodate cooling elements 1 after they have been used.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. An injection system comprising:
    an injection apparatus having a forward end and a rearward end;
    a needle positioned on the injection apparatus at the forward end of the injection apparatus;
    a needle protecting device detachably arranged on the forward end of the injection apparatus, the needle protecting device having a facing end; and
    a cooling element operably coupled to the needle protecting device; wherein
    the cooling element includes a magnetic surface and is operably coupled to the needle protecting device via magnetic attraction.

2. The injection system of claim 1, wherein the cooling element is operably coupled to the facing end of the needle protecting device.

3. The injection system as set forth in claim 1, wherein the cooling element is detachably coupled to the needle protecting device.

4. The injection system as set forth in claim 1, wherein the cooling element comprises a protruding rim.

5. The injection system as set forth in claim 1, wherein the needle protecting device and the cooling element each include an opening through which the needle may pass.

6. The injection system as set forth in claim 1, wherein needle protecting device is formed as a cylinder, the cylinder being closed on the facing side.

7. The injection system as set forth in claim 1, wherein the needle protecting device is movable along the injection apparatus.

8. The injection system as set forth in claim 7, wherein the needle protecting device retracts in the direction of the rearward end of the injection apparatus to expose the needle during an injection.

9. The injection system as set forth in claim 1, further including a coating on an at least one surface of the cooling element.

10. The injection system as set forth in claim 9, wherein the coating is impregnated with a disinfectant.

11. The injection system as set forth in claim 10, wherein evaporation of the disinfectant cools the cooling element.

12. The injection system as set forth in claim 1, wherein the cooling element is provided with an at least one antibacterial surface.

* * * * *